United States Patent
Chau et al.

(10) Patent No.: US 8,305,583 B2
(45) Date of Patent: Nov. 6, 2012

(54) LOCALIZED SURFACE PLASMON RESONANCE SENSING SYSTEM, APPARTATUS, METHOD THEREOF

(75) Inventors: Lai-Kwan Chau, Chiayi (TW);
Wen-Hsin Hsieh, Taipei (TW);
Wei-Ting Hsu, Taipei County (TW);
Po-Liang Chen, Taipei County (TW)

(73) Assignee: National Chung Cheng University, Chia-Yi (TW)

( * ) Notice: Subject to any disclaimer, the term of this patent is extended or adjusted under 35 U.S.C. 154(b) by 424 days.

(21) Appl. No.: 12/647,251

(22) Filed: Dec. 24, 2009

(65) Prior Publication Data

US 2010/0128275 A1    May 27, 2010

Related U.S. Application Data

(63) Continuation-in-part of application No. 11/558,850, filed on Nov. 10, 2006, now abandoned.

(30) Foreign Application Priority Data

Nov. 11, 2005   (TW) ................................ 94139668 A (51) Int. Cl.
*G01N 21/55* (2006.01)
(52) U.S. Cl. ...................................................... 356/445
(58) Field of Classification Search ................... 356/445
See application file for complete search history.

(56) References Cited

U.S. PATENT DOCUMENTS

| 6,579,721 | B1 * | 6/2003 | Natan et al. ............... 436/164 |
| 7,352,468 | B2 * | 4/2008 | Tarsa ............................ 356/445 |
| 2005/0186565 | A1 * | 8/2005 | Malak ........................... 435/5 |
| 2005/0200853 | A1 * | 9/2005 | Mori et al. ................... 356/445 |
| 2009/0066962 | A1 * | 3/2009 | Niwa et al. ................... 356/445 |
| 2010/0093623 | A1 * | 4/2010 | Reed et al. ................... 514/12 |
| 2010/0171958 | A1 * | 7/2010 | Chau et al. ................... 356/445 |
| 2012/0182550 | A1 * | 7/2012 | Tang et al. ................... 356/301 |

* cited by examiner

*Primary Examiner* — Tarifur Chowdhury
*Assistant Examiner* — Michael P Lapage
(74) *Attorney, Agent, or Firm* — WPAT, P.C.; Anthony King (57) ABSTRACT

A sensing system comprises a light source, an optical fiber, a plurality of noble metal nano-particles, a micro-fluidic module and a photo detector. The optical fiber couples an incident light. The plurality of noble metal nano-particles are disposed on a surface of the optical fiber to form a noble metal nano-particle submonolayer, the noble metal nano-particles are substantially separated from each adjacent noble metal nano-particles such that the conductivity of the noble metal nano-particle submonolayer is smaller than that of a metal film. The micro-fluidic module accommodates the optical fiber and a sample, and the sample is driven to contact with the noble metal nano-particles. The photo detector detects an emergent light from the optical fiber. When the incident light interacts with the noble metal nano-particles, a signal derived from localized surface plasmon resonance in form of attenuated light or elastic scattered light is outputted through the photo detector.

17 Claims, 9 Drawing Sheets

LOCALIZED SURFACE PLASMON RESONANCE SENSING SYSTEM, APPARTATUS, METHOD THEREOF

CROSS-REFERENCE TO RELATED APPLICATIONS

This application claims priority to, and is a Continuation-in-part of, U.S. patent application Ser. No. 11/558,850, filed on Nov. 10, 2006, now pending, which claims priority from Taiwan Patent Application No. 094139668 filed on Nov. 11, 2005, which are hereby incorporated by reference in their entirety.

Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of all of the prior art of record and any search that the Office deems appropriate.

BACKGROUND OF THE INVENTION (a) Field of the Invention

The present invention is related to a localized surface plasmon resonance (LSPR) sensing system with noble metal nano-particles on an optical fiber as a transducer, and more particularly, to a LSPR sensing system, apparatus, and method thereof.

(b) Description of the Prior Art

Propagated surface plasmon resonance (PSPR) relates to a phenomenon when an incidence light emitted from a light source reaches the surface of the metal film at a fixed incident angle, the light intensity reflected from a surface of the metal film picked up by a photo detector is approaching zero, i.e., the reflectance of the metal film is approaching zero while the light beam not reflected propagates at a given speed in a direction along the interface and excites the plasmon on the surface of the metal film to resonate. However, light in the sample medium cannot naturally excite PSPR and a high refractive index prism or grating is required for coupling.

The PSPR sensing system is provided according to the PSPR phenomenon described above by having the surface of a prism or a grating coated with a layer of metal film and then the recognition molecule of an analyte is immobilized or attached to the surface of the metal film. Once the analyte in a sample binds with the recognition molecule, the PSPR phenomenon will be undergoing a certain change that reveals and thus detects the interaction status between the recognition molecule and the analyte.

Since the PSPR sensor has high sensitivity and is label-free, thus it allows real-time analysis of interaction between the recognition molecule and the analyte, and furthermore, permits rapid, quantitative, and parallel screening. The PSPR sensor has been widely applied to detection of bio-molecules.

While the development of nano-materials has been becoming a focus of studies in recent years, optoelectronics, communication, and medical instruments are included in the studies because nano-materials have properties totally different from those bulk materials. In this regard, localized surface plasmon resonance (LSPR) sensing system via excitation of noble metal nano-particles when compared with the conventional propagating surface plasmon resonance (PSPR) sensing system may offer additional advantages such as shorter electromagnetic field decay length, smaller pixel size, faster response time, and capability of simultaneous LSPR sensing and surface-enhanced Raman scattering. Moreover, because PSPR is an extrinsic resonance phenomenon, the PSPR sensor requires complicated optical setup and is bulky in size and thus is difficult to be miniaturized and expensive to afford. Today, the roadmap for the development of biosensor is heading for a miniaturized design. Should the biosensor be made in smaller size for easy portability and simpler design of detection method and operation performance, its applications could have been significantly extended.

SUMMARY OF THE INVENTION

To overcome the foregoing shortcoming, an intrinsic resonance phenomenon of free electron waves in metal nano-particles known as localized surface plasmon resonance (LSPR) is considered as a biosensing technique. LSPR is defined as the collective charge density oscillations restricted in the neighborhood of the nano-particles which is excited by an electromagnetic field with a specific frequency, and may be set without utilizing the prism or grating for light coupling. Therefore, very small sensors can be possibly made by using LSPR technique with a simple optical set up. Similar to conventional PSPR, the resonance condition may detect an immediate change in the interfacial refractive index (RI) of the surrounding medium as well as the bio-molecular interactions at the colloid-solution interface. While observing the characteristics of light attenuation, we may find that when the local refractive index around the nano-particles increases, the peak wavelength of the extinction spectrum of the nano-particles will shift to a longer wavelength and the absorbance (or absorption cross-section) will increase. While observing the characteristics of an elastic scattered light, we may find that when the refractive index of the medium rises, the peak wavelength in the light scattering spectrum of the nano-particles also shifts to a longer wavelength and the light scattering intensity (or scattering cross-section) increases. For an optical fiber modified with noble metal nano-particles on the exposed surface of its core, the light at the resonant frequency will interact with the nano-particles to excite the LSPR at the position of each reflection interface. The more the number of times of total internal reflections through the optical fiber, the more significant is the effect on the light intensity at the resonant frequency. Thus, the sensing sensitivity is significantly enhanced.

The LSPR technique is applied to provide a highly sensitive label-free optical biosensor without any bulky optics. The LSPR sensor may be easily fabricated and constructed by simple optical designs. Further, the sensor has the potential capability to be miniaturized for on-site sensing and is disposable.

Accordingly, the primary purpose of the present invention is to provide a localized surface plasmon resonance sensing system, apparatus, and method thereof to further promote sensitivity of the sensing system, and reduce analysis time and consumption of samples and reagents, and decrease the size of the sensing system.

To achieve the purpose, an optical fiber is adapted instead of the conventional prism in the design of the sensing system since the optical fiber provides characteristics of low loss, high frequency band, free of EMI, light-weighted, and small volume for significantly reducing the size of the sensing system. As a micro-fluidic chip is essentially comprised of micro-fluidic parts including micro-fluidic channel, micro-pump, micro-valve, actuator, and micro-sensor to provide multi-task functions such as movement of sample solution, reaction, detection, and sample collection; the micro-fluidic chip is integrated in the present invention to further promote the sensitivity of the sensing system and reduce analysis time and consumption of samples and reagents.

Accordingly, the present invention is related to a localized surface plasmon resonance sensing system, which comprises a light source, an optical fiber, a plurality of noble metal nano-particles, a micro-fluidic module, and at least one photo detector. The light source provides an incident light. The optical fiber couples the incident light. The noble metal nano-particles are disposed on a surface of the unclad portion of the optical fiber to form a noble metal nano-particle submonolayer. For a closest-packed monolayer of spherical nanoparticles on a surface, the absolute surface coverage is 90.7%. The noble metal nano-particles in this system are substantially separated from each adjacent noble metal nano-particles such that the absolute surface coverage is less than 90.7% and forms a submonolayer. As a result, the conductivity of the noble metal nano-particle submonolayer is smaller than that of a metal film, and the conductivity of the noble metal nano-particle submonolayer is smaller than $2 \times 10^3$ $\Omega^{-1} m^{-1}$. For the localized surface plasmon resonance sensing system to achieve optimum performance, the best absolute surface coverage of noble metal nano-particle submonolayer is less than 50%. The micro-fluidic module accommodates the optical fiber and a sample, and the sample is driven to contact with the noble metal nano-particles. The photo detector detects an emergent light from the optical fiber, preferably without using a light collecting device such as a collimating lens or an optical fiber bundle to aid light collection. Wherein when the incident light interacts with the noble metal nano-particles, a signal derived from localized surface plasmon resonance in form of attenuated light or elastic scattered light is outputted through the photo detector.

Accordingly, the present invention is related to a localized surface plasmon resonance sensing method, which comprises the steps of: providing an incident light by a light source; coupling the incident light by the optical fiber; disposing a plurality of noble metal nano-particles on a surface of the unclad portion of the optical fiber, and the noble metal nano-particles being substantially separated from each adjacent noble metal nano-particles such that the conductivity of the noble metal nano-particle submonolayer is smaller than that of a metal film, and the conductivity of the noble metal nano-particle submonolayer being smaller than $2 \times 10^3$ $\Omega^{-1} m^{-1}$; accommodating the optical fiber and a sample in a micro-fluidic module; driving the sample to contact with the noble metal nano-particles; and detecting an emergent light from the optical fiber through at least one photo detector, preferably without using a light collecting device such as a collimating lens or an optical fiber bundle to aid light collection. Wherein when the incident light interacts with the noble metal nano-particles, a signal derived from localized surface plasmon resonance in form of attenuated light or elastic scattered light is outputted through the photo detector.

Accordingly, the present invention is related to a localized surface plasmon resonance sensing apparatus, which comprises an optical fiber, a plurality of noble metal nano-particles, and a micro-fluidic module. The optical fiber couples an incident light. The plurality of noble metal nano-particles are disposed on a surface of the unclad portion of the optical fiber, the noble metal nano-particles are substantially separated from each adjacent noble metal nano-particles such that the conductivity of the noble metal nano-particle submonolayer is smaller than that of a metal film, and the conductivity of the noble metal nano-particle submonolayer is smaller than $2 \times 10^3$ $\Omega^{-1} m^{-1}$. The micro-fluidic module accommodates the optical fiber and a sample, and the sample is driven to contact with the noble metal nano-particles. Wherein when the incident light interacts with the noble metal nano-particles, a signal derived from localized surface plasmon resonance in form of attenuated light or elastic scattered light is outputted through a photo detector.

Whereas the present invention is adapted with noble metal nano-particles on an optical fiber instead of a noble metal film on the conventional prism, the size of the LSPR sensing system is significantly reduced, sensitivity further promoted, analysis time shortened, and consumption of sample and reagents reduced by taking advantage of the micro-fluidic chip.

DETAILED DESCRIPTION OF THE PREFERRED EMBODIMENTS

Figure 1:
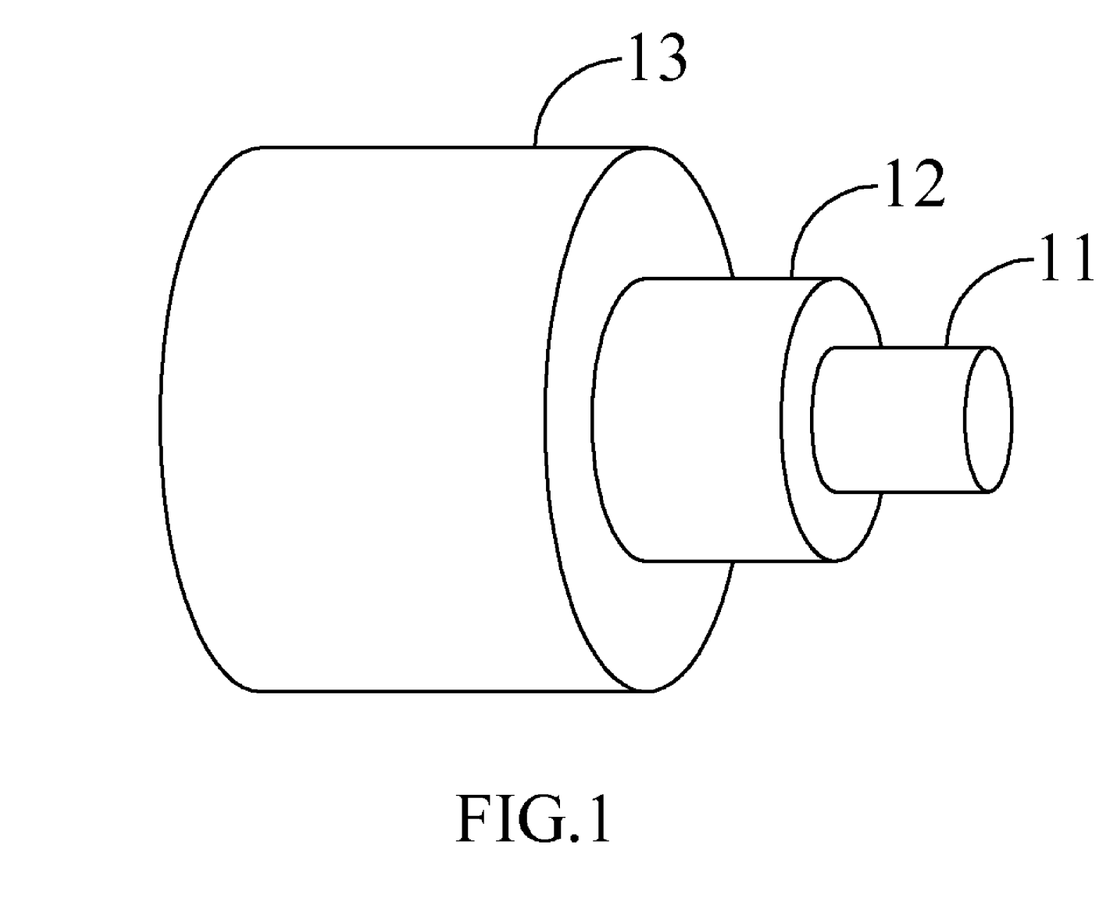
FIG. 1 is a schematic view showing a construction of an optical fiber.
Figure 2:
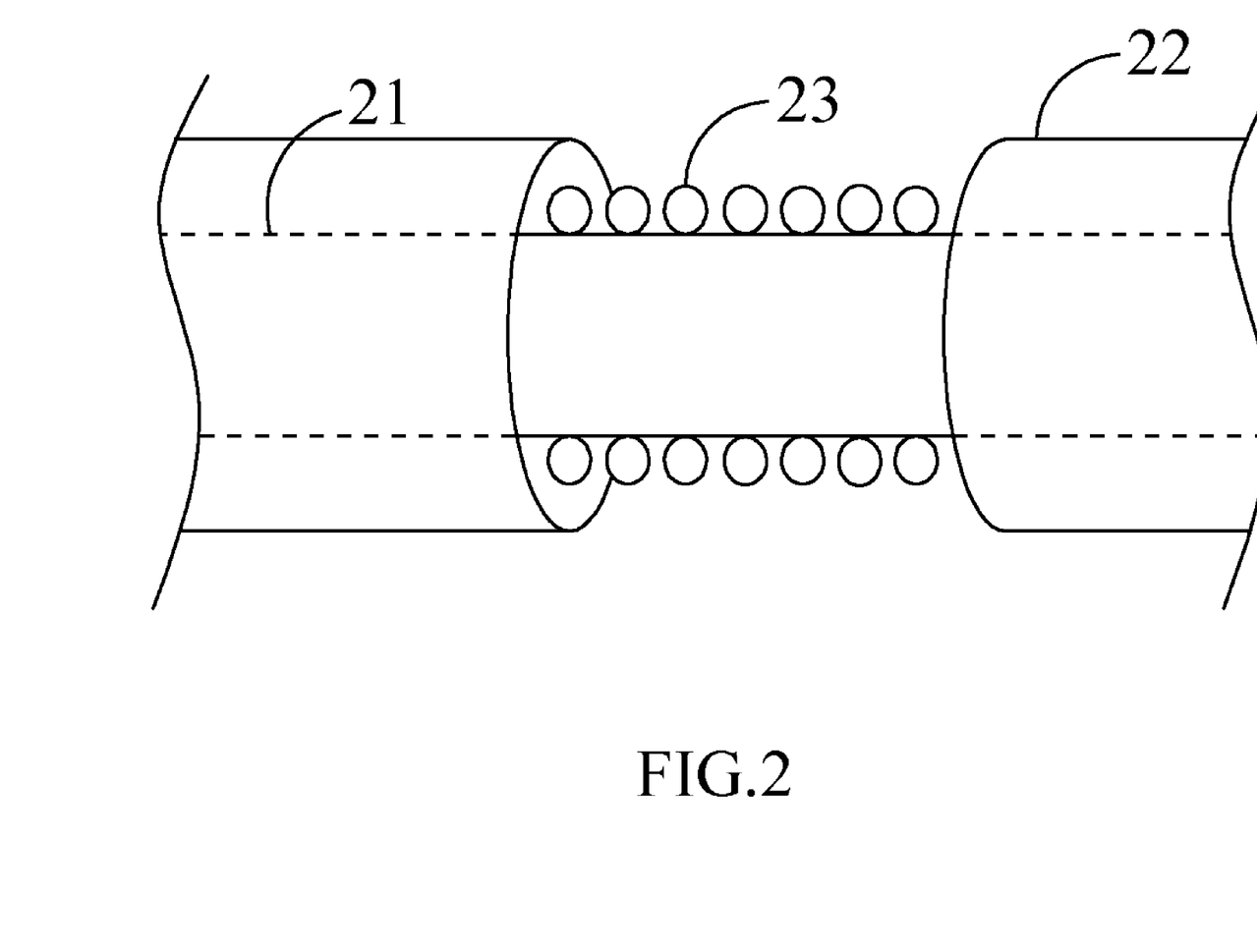
FIG. 2 is a schematic view showing that an optical fiber device where its unclad portion is covered by a submonolayer of noble metal nano-particles.

Referring to FIG. 1 for a schematic view showing construction of an optical fiber cable, the cable is essentially comprised of three layers, respectively the innermost a core 11, a cladding 12 in the middle, an outermost buffer 13 with materials and functions different from one another. As illustrated in FIG. 2 for a schematic view showing that a plurality of noble metal nano-particles 23 are disposed on the unclad portion of an optical fiber. The plurality of noble metal nano-particles 23 are gold nano-particles or silver nano-particles. The optical fiber comprises a stripped area formed by partially removing the cladding 22 of the optical fiber, then the plurality of noble metal nano-particles 23 are disposed on the core 21 of the optical fiber. The noble metal nano-particles 23 are substantially separated from each adjacent noble metal nano-particles such that the conductivity of the noble metal nano-particle submonolayer is smaller than that of the metal film.

Please refer to Table 1, which shows the conductivities of bulk metals at 330 K. The conductivities of the bulk metals are about $10^6 \sim 10^7$ $\Omega^{-1} m^{-1}$. Please refer to Table 2, which shows the conductivities of gold nano-particle (AuNP) layers and gold metal film. Comparing Table 1 with Table 2, when gold (Au) is evaporated to form a gold metal film, the conductivity of the gold metal film is about $10^7$ $\Omega^{-1} m^{-1}$. The value of the conductivity of gold in Table 1 and Table 2 is matching with each other. From Table 2, the conductivities of noble metal nano-particle submonolayer and multilayer are smaller than $2\times10^3 \Omega^{-1}\mathrm{m}^{-1}$. It should be noted that at the surface density of $7\times10^{11}$ particles/cm$^2$, a gold nano-particle submonolayer is formed with an absolute surface coverage of about 67% and the measured resistance exceeds the highest resistance value that can be measured. While at the surface density of $40\times10^{11}$ particles/cm$^2$, a gold nano-particle multilayer is formed and the absolute surface coverage is about 380%. Above all, the conductivities of the noble metal nano-particle submonolayer and multilayer are much smaller than that of the metal film. In other words, the noble metal nano-particle submonolayer may be not deemed to be a conductive metal layer in this present invention.

TABLE 1

Conductivities of Bulk Metals (~300K)

| Metals | Conductivity ($\Omega^{-1} \cdot \mathrm{m}^{-1}$) |
| --- | --- |
| aluminum | $3.77 \times 10^7$ |
| copper | $5.85 \times 10^7$ |
| gold | $4.52 \times 10^7$ |
| iron | $1.04 \times 10^7$ |
| lead | $4.81 \times 10^6$ |
| palladium | $9.49 \times 10^6$ |
| platinum | $9.52 \times 10^6$ |
| plutonium | $7.07 \times 10^5$ |
| silver | $6.29 \times 10^7$ |

TABLE 2

Conductivities of Different Thin Layers

| Thin layers (surface density, particles/cm$^2$ or thickness, nm) | Conductivity ($\Omega^{-1} \cdot \mathrm{m}^{-1}$) |
| --- | --- |
| 11-nm AuNP ($7 \times 10^{11}$ particles/cm$^2$) | $<1.1 \times 10^1$ |
| 11-nm AuNP ($40 \times 10^{11}$ particles/cm$^2$, cross-linked by 2-mercaptoethylamine) | $1.1 \times 10^3$ |
| Au evaporation (70 nm) | $2.0 \times 10^7$ |

The present invention is related to a sensing system integrating the noble metal nano-particles-modified optical fiber with a micro-fluidic chip. Wherein, the micro-fluidic chip is essentially comprised of micro-fluidic parts including micro-fluidic channel, micro-pump, micro-valve, actuator, and micro-sensor to provide multi-task functions such as movement of sample solution, reaction, detection, and sample collection. With the integrated micro-fluidic chip, the present invention further promotes the sensitivity of the sensing system and shortens the analysis time.

Figure 3:
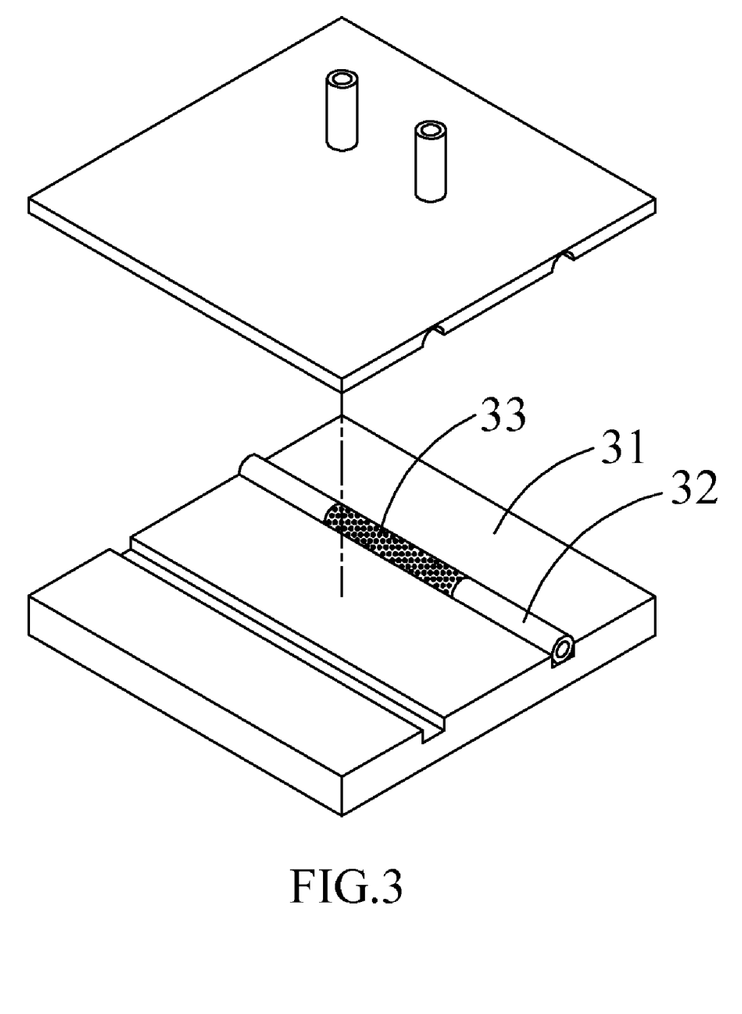
FIG. 3 is a schematic view showing that a micro-fluidic chip is applied to the optical fiber sensing system.

As illustrated in FIG. 3, the micro-fluidic chip may be applied to an optical fiber sensing system. A micro-fluidic chip 31 further comprises at least one fluidic channel to accommodate the sample and the optical fiber 32 and drives the sample to contact with the surface of the noble metal nano-particles 33. It is not limited that only one channel and one optical fiber may be used in the micro-fluidic chip, a multiple channel design may also be used in the micro-fluidic chip for accommodating the plurality of optical fibers. By disposing multiple channels in a micro-fluidic chip, the sensing system may sense multiple samples at the same time. Wherein, the channel has a diameter about 10 μm~2 mm. The micro-fluidic chip further comprises a cover, and the cover includes at least one inlet and at least one outlet. The inlet is used for inputting the sample or reagent, and the outlet is used for outputting the sample or reagent. For the purpose of efficient mass transfer, a pump may be used in the sensing system to accelerate the sample or reagent to pass through the fluidic channels.

Figure 4:
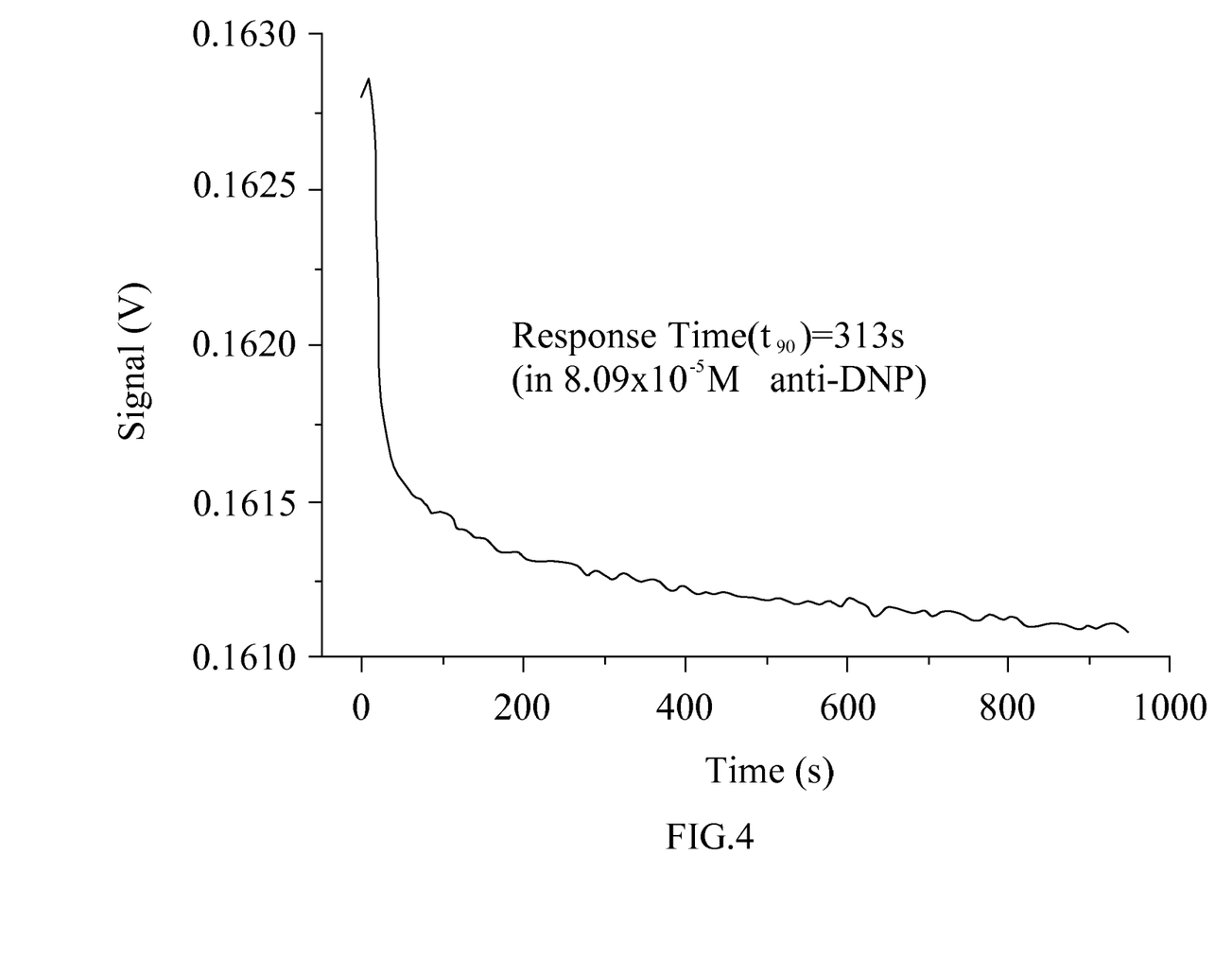
FIG. 4 is a diagram of the signal-time relationship by applying the above micro-fluidic chip as shown in FIG. 3 to this present invention.

Please refer to FIG. 4, which shows a diagram of the signal-time relationship by applying the above micro-fluidic chip as shown in FIG. 3 to this present invention. In order to sense Anti-DNP in a sample, the recognition unit is DNP (=Dinitrophenyl antigen), which is functionalized on the surface of the gold nano-particles. Wherein, the solution of Anti-DNP with $8.09\times10^{-5}$ M is used in this embodiment. When the analyte (Anti-DNP) is inputted from the inlet, the analyte will bind with DNP on the surface of the gold nano-particles. When the incident light interacts with the gold nano-particles, a signal derived from localized surface plasmon resonance in form of attenuated light is outputted through the photo detector. Herein, the response time is about 313 seconds.

Figure 5:
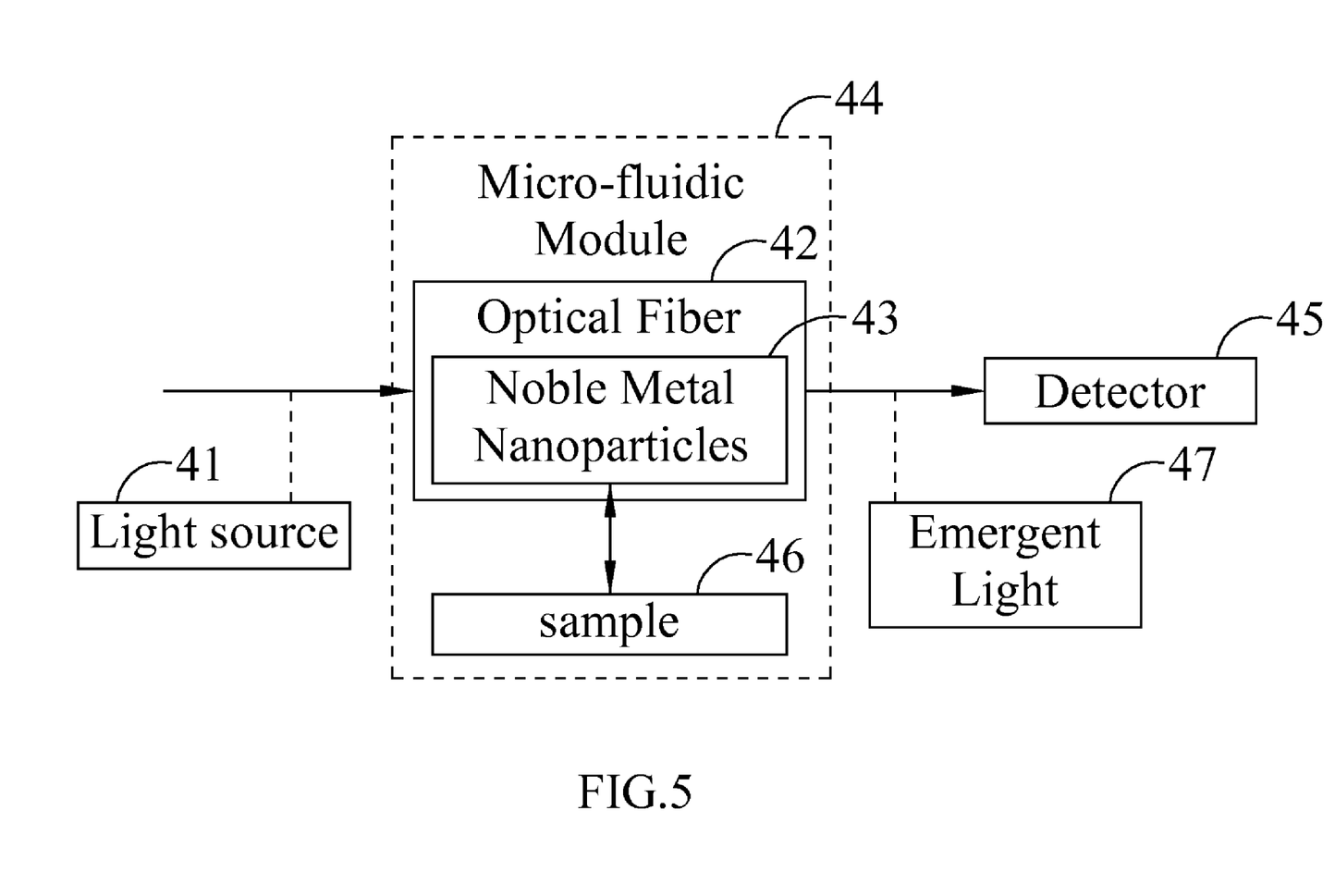
FIG. 5 is a block chart of a localized surface plasmon resonance sensing system of the present invention.
Figure 6:
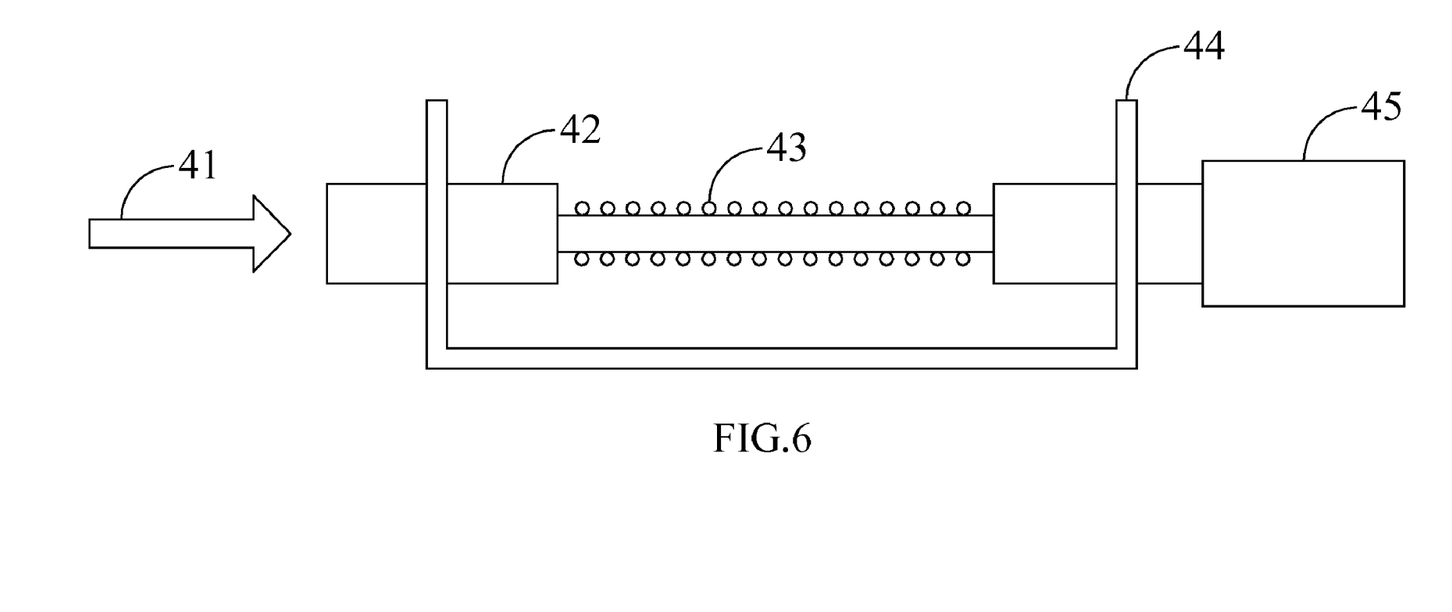
FIG. 6 is a schematic view showing a preferred embodiment of the present invention.

Now referring to FIGS. 5 and 6 respectively a block diagram and a cross sectioned view of a preferred embodiment of the present invention, the system includes a light source 41, an optical fiber 42, a plurality of noble metal nano-particles 43, a micro-fluidic module 44, and a photo detector 45. Wherein, the light source 41 may be a laser, such that the light source 41 provides the incident light with a single frequency. The light source 41 may also be a light-emitting diode (LED), such that the light source provides the incident light with a narrow frequency band. The optical fiber 42 couples the incident light, and the noble metal nano-particles are disposed on the stripped area of the optical fiber 42. The noble metal nano-particles 43 are comprised of gold or silver nano-particles disposed on the unclad surface of the optical fiber 42; the micro-fluidic module 44 is related to a micro-fluidic chip to accommodate the optical fiber 42 and a sample 46 and drives the sample 46 to get contact with the noble metal nano-particles 43; the photo detector 45 may be a photodiode, phototransistor, or PMT, and the photo detector 45 operates to detect the intensity of an emergent light 47 from the optical fiber 42; and the emergent light 47 may be a transmitted light, a reflected light, or a leaked light from the unclad region. The transmitted light is defined as the emergent light exiting the distal end of the optical fiber; the reflected light is defined as the emergent light exiting the proximal end of the optical fiber; while the leaked light is defined as the elastic scattered light emerged from the unclad region. Furthermore, the emergent light 47 is not a fluorescent light. Because the photo detector 45 directly detects the light intensity of the emergent light, a polarizer or analyzer is not disposed between the optical fiber and the photo detector to polarize the emergent light in the sensing system and a wavelength selection device is not disposed between the optical fiber and the photo detector to measure the spectrum of the emergent light. From which, it will reduce the size and cost of the sensing system in the present invention.

Figure 7:
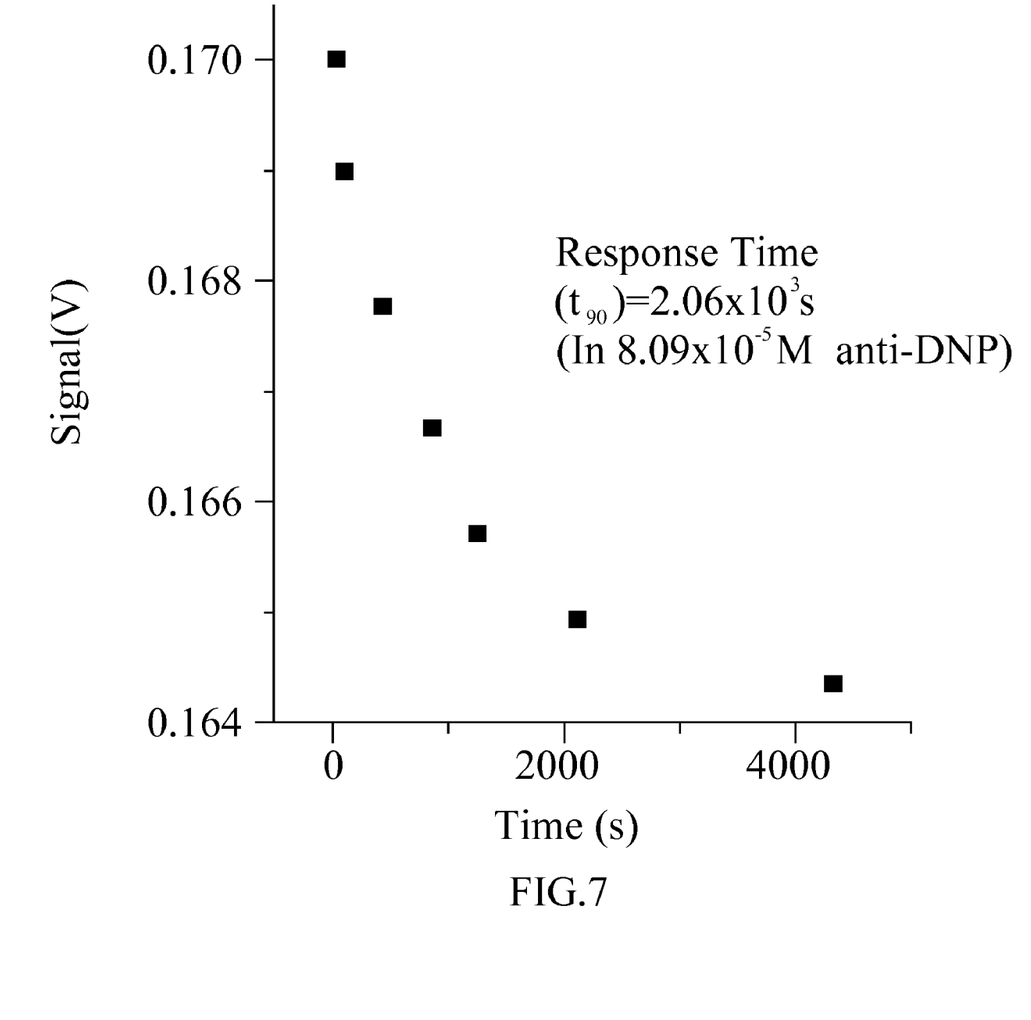
FIG. 7 is a diagram of the signal-time relationship by applying the above noble metal nanoparticles-modified optical fiber as shown in FIG. 2 to the sensing system with a conventional liquid container.

Please refer to FIG. 7, which shows a diagram of the signal-time relationship by using the gold nanoparticles-modified optical fiber as shown in FIG. 2 in the sensing system but a conventional liquid container is used instead of the micro-fluidic chip. In order to sense Anti-DNP, the recognition unit is DNP (=Dinitrophenyl antigen), which is functionalized on the surface of gold nano-particles. Wherein, a solution of Anti-DNP with $8.09\times10^{-5}$ M is used in this embodiment. When the analyte (Anti-DNP) is inputted in the container, the analyte will bind with DNP on the surface of the gold nano-particles. When the incident light interacts with the gold nano-particles, a signal derived from localized surface plasmon resonance in form of attenuated light is outputted through the photo detector. Herein, the response time is approximately $2.06\times10^3$ seconds.

Above all, the response time in the sensing system with the micro-fluid module is about 313 s, and the response time in the sensing system with the container is about $2.06\times10^3$ s. The sensing system with micro-fluid module has better sensibility than the sensing system with the conventional container. When the optical fiber is integrated with the micro-fluid module, then there will be an improvement in the performance of a bio-sensing system.

Figure 8:
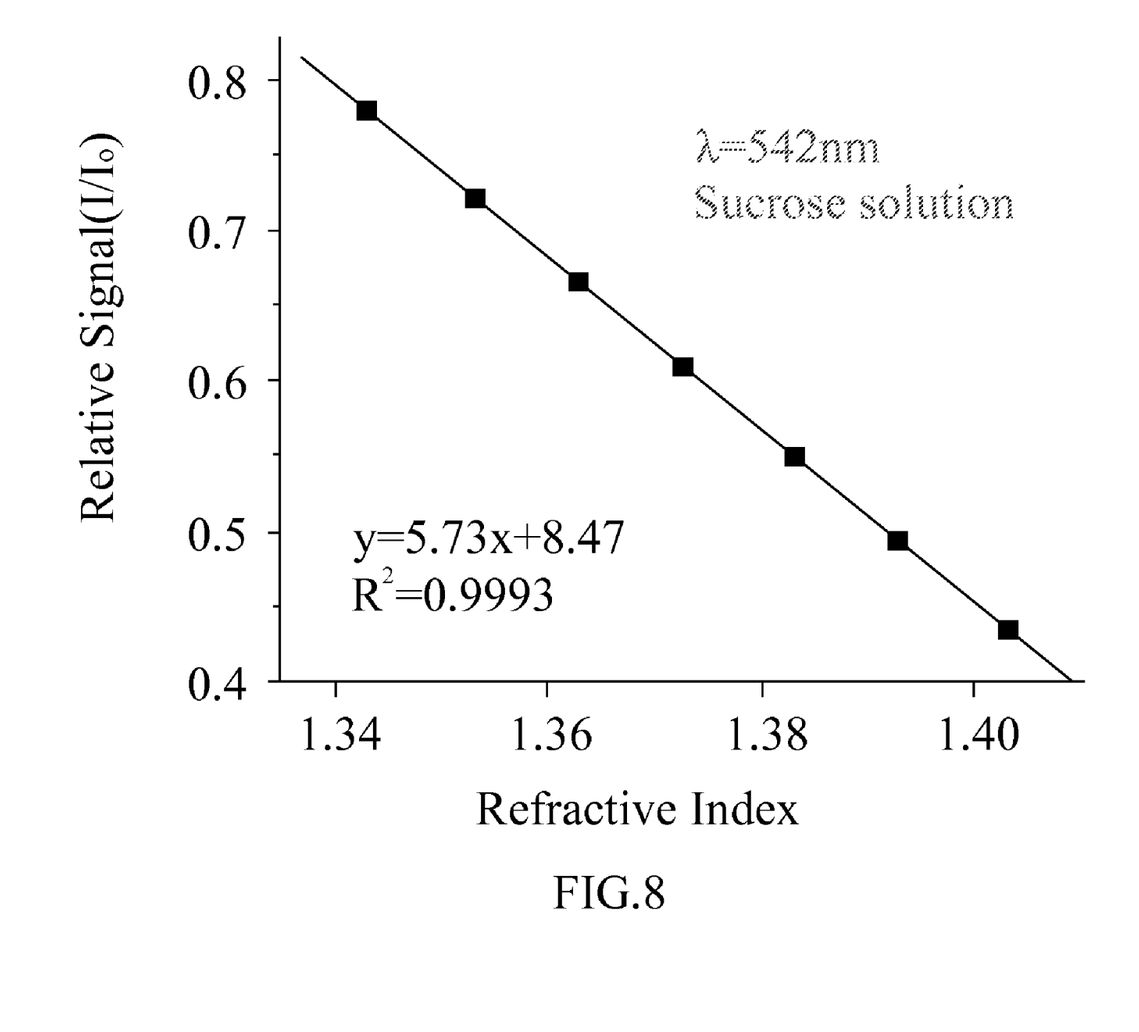
FIG. 8 is a diagram of the relative signal ($I/I_0$)-refractive index relationship obtained by this present invention.

As illustrated in FIG. 8, is shown a diagram of the relative signal ($I/I_0$)-refractive index relationship obtained by this present invention. Wherein the incident light has a wavelength of 542 nm, and the sample is a sucrose solution in this embodiment. It demonstrates a linear relationship between the relative signal and the solution refractive index. Herein the sensitivity of this embodiment is 4.2 AU/RIU, the refractive index resolution of this embodiment is about $10^{-5}$ RIU. The sensitivity of this embodiment is significantly enhanced as compared to that of a similar gold nano-particle submonolayer on a glass slide interrogated via transmission mode, which has a sensitivity of 0.46 AU/RIU.

Figure 9:
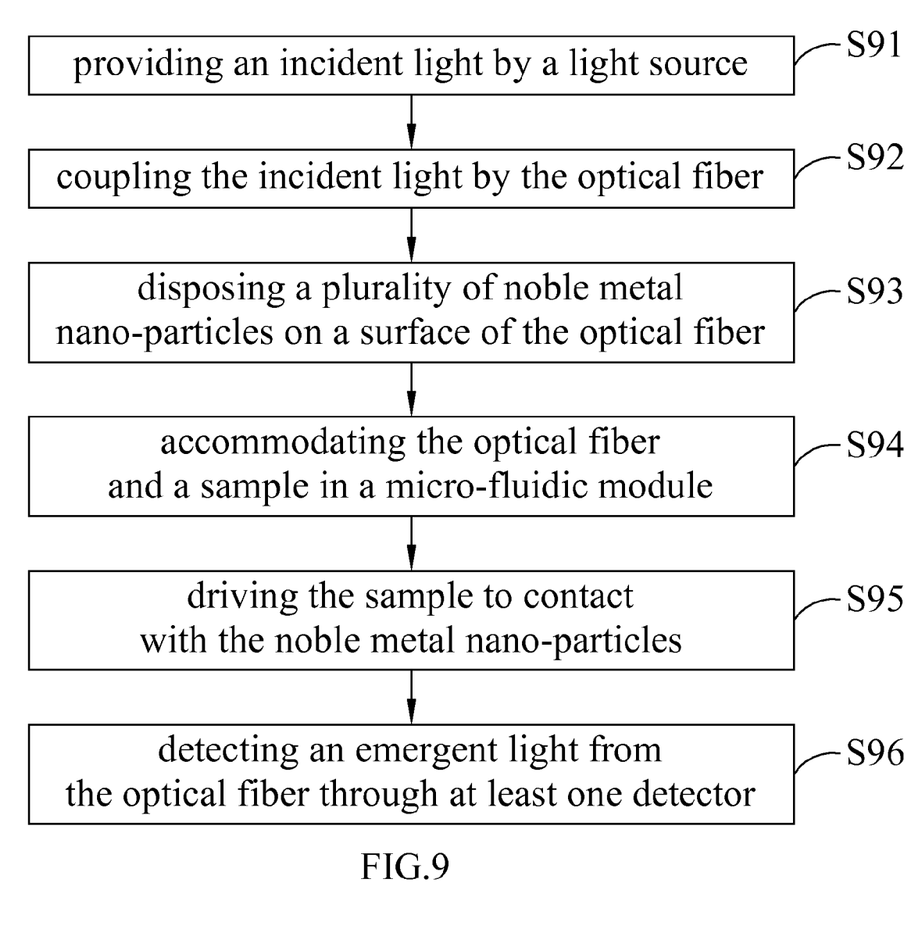
FIG. 9 is a process flow chart of the localized surface plasmon resonance sensing method of the present invention.

As illustrated in FIG. 9 is the process flow chart of the LSPR sensing method of the present invention, the process includes the following steps: STEP S91, providing an incident light by a light source; STEP S92, coupling the incident light by the optical fiber; STEP S93, disposing a plurality of noble metal nano-particles on a surface of the unclad portion of the optical fiber, and the noble metal nano-particles is substantially separated from each adjacent noble metal nano-particles such that the conductivity of the noble metal nano-particle submonolayer is smaller than that of a metal film, and the conductivity of the noble metal nano-particle submonolayer is smaller than $2\times10^3$ $\Omega^{-1}m^{-1}$; STEP S94, accommodating the optical fiber and a sample in a micro-fluidic module; STEP S95, driving the sample to contact with the noble metal nano-particles; STEP S96, detecting an emergent light from the optical fiber through at least one photo detector, preferably without using a light collecting device such as a collimating lens or an optical fiber bundle to aid light collection; wherein when the incident light interacts with the noble metal nano-particles, a signal derived from localized surface plasmon resonance in form of attenuated light or elastic scattered light is outputted through the photo detector.

The localized surface plasmon resonance (LSPR) sensing system is constructed with a submonolayer of the noble metal nano-particles, and the propagated surface plasmon resonance (PSPR) sensing system is constructed with a conductive metal film. The PSPR is not intrinsically resonant and requires a prism or grating to excite surface plasmons which act as a damping mechanism on a reflected or transmitted optical beam with relatively sharp wavelength and angular dependence, which is highly dependent on the local refractive index at the interface. The LSPR is also highly dependent on the local refractive index at the surface of the noble metal nano-particles, but is intrinsically resonant and can be directly excited, thus leading to a shift in the peak wavelength and cross-section in the spectra of absorption and elastic scattering.

It is to be noted that the preferred embodiments disclosed in the specification and the accompanying drawings are not limiting the present invention; and that any construction, installation, or characteristics that is same or similar to that of the present invention should fall within the scope of the purposes and claims of the present invention.

What is the claim is:

1. A localized surface plasmon resonance sensing system, comprising:
    a light source providing an incident light;
    an optical fiber coupling the incident light, wherein there is not a polarizer or a microscope objective between the light source and the optical fiber;
    a plurality of noble metal nano-particles being disposed on a surface of the optical fiber in an unclad region to form a noble metal nano-particle submonolayer, the noble metal nano-particles being substantially separated from each adjacent noble metal nano-particles such that the conductivity of the noble metal nano-particle submonolayer is smaller than that of a metal film, and the conductivity of the noble metal nano-particle submonolayer being smaller than $2\times10^3$ $\Omega^{-1}m^{-1}$.
    a micro-fluidic module accommodating the optical fiber and a sample, and the sample being driven to contact with the noble metal nano-particles; and
    at least one photo detector detecting a light intensity of an emergent light from the optical fiber without using any light collecting device or polarizer or microscope objective or spectral filter to aid light collection, wherein the emergent light is a transmitted light, a reflected light, or a leaked light from the unclad region and the emergent light is not a fluorescent light, and the photo detector directly detects the light intensity of the emergent light;
    wherein when the incident light interacts with the noble metal nano-particles, a signal derived from localized surface plasmon resonance in the form of attenuated light or elastic scattered light is outputted through the photo detector.

2. The localized surface plasmon resonance sensing system as claimed in claim 1, wherein the light source provides the incident light with a single frequency or a narrow frequency band.

3. The localized surface plasmon resonance sensing system as claimed in claim 1, wherein the noble metal nano-particles are disposed at a stripped area, and the stripped area is formed by removing a cladding of the optical fiber partially.

4. The localized surface plasmon resonance sensing system as claimed in claim 1, wherein the noble metal nano-particles are gold nano-particles or silver nano-particles.

5. The localized surface plasmon resonance sensing system as claimed in claim 1, wherein the micro-fluidic module further comprises at least one inlet and at least one outlet, the inlet is disposed for inputting the sample, and the outlet is disposed for outputting the sample.

6. The localized surface plasmon resonance sensing system as claimed in claim 1, wherein the noble metal nano-particles are further modified with a recognition molecule for sensing an analyte in the sample.

7. A localized surface plasmon resonance sensing method comprising the steps of:
    providing an incident light by a light source;
    coupling the incident light by an optical fiber, wherein there is not a polarizer or a microscope objective between the light source and the optical fiber;
    disposing a plurality of noble metal nano-particles on a surface of the optical fiber in an unclad region, and the noble metal nano-particles being substantially separated from each adjacent noble metal nano-particles such that the conductivity of the noble metal nano-particle submonolayer is smaller than that of a metal film, and the conductivity of the noble metal nano-particle submonolayer being smaller than $2\times10^3$ $\Omega^{-1}m^{-1}$;
    accommodating the optical fiber and a sample in a microfluidic module;
    driving the sample to contact with the noble metal nano-particles; and
    detecting a light intensity of an emergent light from the optical fiber through at least one photo detector without using any light collecting device or polarizer or microscope objective or spectral filter to aid light collection, wherein the emergent light is a transmitted light, a reflected light, or a leaked light from the unclad region, and the emergent light is not a fluorescent light, and the photo detector directly detects the light intensity of the emergent light;

wherein when the incident light interacts with the noble metal nano-particles, a signal derived from localized surface plasmon resonance in the form of attenuated light or elastic scattered light is outputted through the photo detector.

8. The localized surface plasmon resonance sensing method as claimed in claim 7, wherein the light source provides the incident light with a single frequency or a narrow frequency band.

9. The localized surface plasmon resonance sensing method as claimed in claim 7, further comprising the step of: disposing the noble metal nano-particles at a stripped area; wherein the stripped area is formed by removing a cladding of the optical fiber partially.

10. The localized surface plasmon resonance sensing method as claimed in claim 7, wherein the noble metal nano-particles are gold nano-particles or silver nano-particles.

11. The localized surface plasmon resonance sensing method as claimed in claim 7, wherein the micro-fluidic module further comprises at least one inlet and at least one outlet, the inlet is disposed for inputting the sample, and the outlet is disposed for outputting the sample.

12. The localized surface plasmon resonance sensing method as claimed in claim 7, wherein the noble metal nano-particles are further modified with a recognition molecule for sensing an analyte in the sample.

13. A localized surface plasmon resonance sensing apparatus, comprising:

an optical fiber coupling an incident light, wherein the incident light does not pass any polarizer or microscope objective;

a plurality of noble metal nano-particles being disposed on a surface of the optical fiber in an unclad region, the noble metal nano-particles being substantially separated from each adjacent noble metal nano-particles such that the conductivity of the noble metal nano-particle sub-monolayer is smaller than that of a metal film, and the conductivity of the noble metal nano-particle submonolayer being smaller than $2 \times 10^3 \ \Omega^{-1} m^{-1}$; and a micro-fluidic module accommodating the optical fiber and a sample, and the sample being driven to contact with the noble metal nano-particles;

wherein when the incident light interacts with the noble metal nano-particles, a signal derived from localized surface plasmon resonance in the form of attenuated light or elastic scattered light is outputted through a photo detector, and the photo detector detects a light intensity of an emergent light from the optical fiber without using any light collecting device or polarizer or microscope objective or spectral filter to aid light collection, wherein the emergent light is a transmitted light, a reflected light, or a leaked light from the unclad region, and the emergent light is not a fluorescent light, and the photo detector directly detects the light intensity of the emergent light.

14. The localized surface plasmon resonance sensing apparatus as claimed in claim 13, wherein the noble metal nano-particles are disposed at a stripped area, and the stripped area is formed by removing a cladding of the optical fiber partially.

15. The localized surface plasmon resonance sensing apparatus as claimed in claim 13, wherein the noble metal nano-particles are gold nano-particles or silver nano-particles.

16. The localized surface plasmon resonance sensing apparatus as claimed in claim 13, wherein the micro-fluidic module further comprises at least one inlet and at least one outlet, the inlet is disposed for inputting the sample, and the outlet is disposed for outputting the sample.

17. The localized surface plasmon resonance sensing apparatus as claimed in claim 13, wherein the noble metal nano-particles are further modified with a recognition molecule for sensing an analyte in the sample.

* * * * *